United States Patent
Takahashi et al.

(10) Patent No.: US 8,343,427 B2
(45) Date of Patent: Jan. 1, 2013

(54) BIOSENSOR

(75) Inventors: Mie Takahashi, Ehime (JP); Ryoko Kawamata, Ehime (JP)

(73) Assignee: Panasonic Corporation, Osaka (JP)

( * ) Notice: Subject to any disclaimer, the term of this patent is extended or adjusted under 35 U.S.C. 154(b) by 8 days.

(21) Appl. No.: 12/993,686

(22) PCT Filed: May 21, 2009

(86) PCT No.: PCT/JP2009/002235
§ 371 (c)(1),
(2), (4) Date: Nov. 19, 2010

(87) PCT Pub. No.: WO2009/144894
PCT Pub. Date: Dec. 3, 2009

(65) Prior Publication Data
US 2011/0070634 A1  Mar. 24, 2011

(30) Foreign Application Priority Data
May 26, 2008 (JP) .................................. 2008-136143

(51) Int. Cl.
*G01N 15/06* (2006.01)
*G01N 33/00* (2006.01)
*G01N 33/48* (2006.01)

(52) U.S. Cl. ........................ 422/82.01; 422/50; 422/68.1
(58) Field of Classification Search .................... 422/50, 422/68.1, 82.01
See application file for complete search history.

(56) References Cited

U.S. PATENT DOCUMENTS

| 5,997,817 A | 12/1999 | Crismore et al. |
| 2002/0027072 A1 | 3/2002 | Cui et al. |

FOREIGN PATENT DOCUMENTS

| JP | 08-075748 | 3/1996 |
| JP | 2001-526388 | 12/2001 |
| JP | 2002-090331 | 3/2002 |
| JP | 2005-205587 | 8/2005 |
| JP | 2007-212215 | 8/2007 |
| WO | 01/04614 | 1/2001 |

*Primary Examiner* — Brian J Sines
(74) *Attorney, Agent, or Firm* — Hamre, Schumann, Mueller & Larson P.C.

(57) ABSTRACT

An inexpensive biosensor is provided that can realize an electrochemical analysis and perform measurement with high accuracy or convenience. The biosensor is an immunological sensor that enables measurement anywhere at anytime by anyone while keeping convenience. The biosensor includes: an electrode sensor unit 4 in which an electric conductive layer 2 is provided on an electrode-unit forming substrate 1 having an insulating property and an electrode portion 3 for detecting an electrochemical signal is formed on the electrode-unit forming substrate 1; and a chromatographic sensor unit 10 in which an extended layer 7 including a porous film for extending a specimen solution is provided on an extended-portion forming substrate 6, wherein the electrode sensor unit 4 and the chromatographic sensor unit 10 are stacked with the extended-portion forming substrate 6 interposed between the electrode sensor unit 4 and the chromatographic sensor unit 10.

5 Claims, 4 Drawing Sheets

BIOSENSOR

TECHNICAL FIELD

The present invention relates to a biosensor such as an immuno-chromatographic sensor that has an electrode enabling electrochemical measurement.

BACKGROUND ART

In recent years, home care and community health care in a doctor's office and a clinic have improved and the number of early diagnoses and the number of urgent laboratory tests have increased. Against this backdrop, analyzing devices have been demanded that can quickly and easily perform measurement with high accuracy even if users are not medical technologists. Thus small analyzing devices for POCT (Point of Care Testing) have received attention that can perform reliable measurement in a short time without complicated operations.

POCT is a generic name of inspections conducted in locations "close to patients", for example, in consulting rooms of practitioners and specialists, hospitals, and clinics for outpatients. POCT has been a notable method that is useful for improving the quality of diagnoses such that a doctor quickly judges an inspection result, immediately performs treatment, and monitors the process of the treatment and the prognosis. Inspections conducted by such small analyzing devices can reduce the cost of transporting specimens, the cost of equipment, and the cost of unnecessary inspections, thereby reducing the total inspection cost as compared with inspections conducted in central examination rooms. In the U.S. featuring rational hospital management, a POCT market has rapidly expanded and is expected to grow worldwide, including Japan.

In a dry-type biosensor (analysis element) typified by an immuno-chromatographic sensor, an adjustment of a reagent is not necessary and a target analyte contained in a liquid sample can be analyzed only by a simple operation, e.g., dropping of the liquid sample (specimen solution) such as blood and urine to be measured into the biosensor. Currently, a large number of dry-type biosensors have been put into practical use as representative POCT biosensors because dry-type biosensors are quite useful for easily and quickly analyzing a target analyte in a liquid sample.

In an immuno-chromatographic sensor using an antigen-antibody reaction, detection involves high specificity and a strong binding force. Thus in an analysis of quite a low concentration of a bioactive substance, an immuno-chromatographic sensor demonstrates more excellent properties than other kinds of sensors. Such an immuno-chromatographic sensor includes, on a porous carrier such as nitrocellulose and glass fiber filter paper, a reaction portion in which a reagent to be bound specifically to a target analyte is immobilized; a labeled reagent retaining portion labeled with a reagent bound specifically to the target analyte and an immobilized reagent; and a sample adding portion in which a liquid sample is added to the labeled reagent retaining portion or upstream of the labeled reagent retaining portion in a sample extending direction. The following will discuss the measurement principle. First, the liquid sample is added to the sample adding portion (specimen solution supply portion). The added liquid sample is extended on the porous carrier and reaches the labeled reagent retaining portion. After that, the liquid sample is extended downstream, passes through a reaction layer, and is extended downstream on the porous carrier. In the case where the liquid sample contains a target analyte, the target analyte first reacts specifically with a labeled reagent and then is extended to the reaction portion. When reaching the reaction portion, the target analyte having reacted specifically with the labeled reagent also reacts specifically with the immobilized reagent of the reaction portion, resulting in a color reaction depending on the concentration of the target analyte. Thus by analyzing the color reaction, the concentration of the target analyte can be confirmed. By using this principle, many diagnostic agents of pregnancy, cancer markers, cardiac markers, and the like have been put into practical use and are available on the market. The measurement principle was described according to, e.g., a sandwich reaction. A competitive reaction may be used for measurement.

In many immuno-chromatographic sensors, quantitative decisions are mainly made. In recent years, some products have been developed to quantitatively measure the concentration of a target analyte according to the degree of a color reaction in a reaction portion by using a reader, like diagnostic agents of cardiac markers. An optical phenomenon is mainly used as a principle of quantitative measurement. In frequently used methods, a color is generated by interaction between a target analyte and a specific protein immobilized on a chromatographic carrier of a porous film and the intensity of the color is optically detected by a detector.

In the case of quantitative measurement using an immuno-chromatographic sensor, however, information is obtained only by optically reading the degree of a color in a reaction portion. Thus just a few pieces of information are obtained and it is difficult to conduct quantitative measurement with higher accuracy.

For this reason, various methods have been used in which the number of pieces of information is increased by electrochemical techniques. For example, Patent Literature 1 describes a biosensor that is an immuno-chromatographic sensor of lateral flow type. The biosensor is made up of an electrode part and a chromatography matrix part having an electrode formed of silver/silver chloride paste ink on a printing substrate that is pure cellulose chromatography paper.

In this method, the biosensor is fabricated by forming the electrode part on a preformed porous film by screen printing. In screen printing, a printing paste prepared with an organic solvent is frequently used. However, many porous films are deformed by the penetration of organic solvents, so that the porous shape may be broken. Therefore, the porous shape of the porous film may be broken by forming the electrode by screen printing and the porous film cannot act as expected. Thus the selection of a solvent is quite important in the printing of an electrode on a porous film.

Even when a selected paste material does not hamper printing, a printing paste coming inside a porous film may cause clogging, so that a specimen solution may be insufficiently extended or the specimen solution may not penetrate into a hydrophobic paste material. It is quite difficult to perform printing while avoiding these problems.

Further, in the case where an electrode is formed by screen printing, a paste bleeding in printing varies a measurement electrode area, disadvantageously causing variations in response characteristics. The occurrence of this problem is extremely high in Patent Literature 1 in which the electrode is formed on the porous film. Thus this serious problem should be solved to improve quantitative accuracy in the biosensors using carriers of porous films. Only measuring electrodes of equal areas may be selected but the selection of such measuring electrodes may reduce the yield, resulting in high cost.

In order to solve these problems, it is essential as an inspection process to measure an electrode area after printing on a porous film. The addition of the inspection process slightly improves the measurement accuracy of the biosensor but increases the number of steps and the manufacturing cost of the biosensor, so that even if the performance of sensors improves, it is impossible to provide inexpensive biosensors. For this reason, it has been strongly requested to provide inexpensive materials enabling electrochemical analyses with uniform performance. Another problem is that the formation of an electrode on a biosensor by screen printing makes it impossible to read an optical signal in a reaction portion, though an electrochemical measurement method can be realized.

Patent Literature 2 describes an electrode immune-response analyzing device of a flow-through type in which an upper cover having a sample inlet, an upper filter, first and second impregnating portions, a passage member, an electrode portion formed on an electrode substrate, a specific binding substance insolubilizing film, an absorbing portion, and a lower substrate are stacked in the thickness direction and a sample is passed in the thickness direction (stacking direction). In this method, the specific binding-substance insolubilizing porous film is not bonded but is stacked on an electrode formed by screen printing on the electrode substrate made of PET. The amount of a substance having undergone a specific binding reaction on the porous film is quantitatively measured by determining, on the electrode, the amount of current obtained from an enzyme-labeled antibody. Unlike in Patent Literature 1 in which the electrode is directly formed on the porous film, the electrode and the porous film are separately fabricated in this configuration and thus the porous film is not directly coated with a printing paste. It is therefore possible to prevent the porous film from being seriously broken, increase the selection of printing pastes for printing the electrode portion, and reduce the occurrence of variations in an electrode area in the event of blurred printing. However, unless the specific binding-substance insolubilizing porous film and the electrode that have been separately prepared are stacked with high accuracy, it is not possible to achieve high-accuracy measurement. Further, in this system, measurement is conducted by reading an electrochemical signal obtained by an enzyme reaction and thus a two-step reaction is necessary in which the amount of a substance having undergone a specific binding reaction is read by the enzyme reaction. Consequently, the quantitative accuracy may be affected by two factors that are variations caused by a specific binding reaction and response variations caused by an enzyme reaction.

Patent Literature 3 describes a biosensor including a porous thin film on the surface of an electrode. In this biosensor, a collected whole blood sample is chromatographically moved by the porous thin film to separate plasma from the whole blood and only the plasma is measured in contact with an electrode system. Since only the plasma is separated, the influence of hematocrit in blood is eliminated. In measurement, however, a sufficient time is necessary between the separation of the plasma and the contact with the electrode system and the accuracy of separation is not enough to fully separate the plasma. Thus the quantitative accuracy is not so improved, though the influence of hematocrit is reduced.

Citation List

Patent Literature

Patent Literature 1: International Publication No. WO01/004614

Patent Literature 2: Japanese Patent Laid-Open No. 8-75748

Patent Literature 3: Japanese Patent Laid-Open No. 2002-90331

SUMMARY OF INVENTION

Technical Problem

As has been discussed, the biosensors or analyzing devices according to Patent Literature 1 to 3 are devised to electrochemically perform detection and quantification in the biosensors where an immune reaction basically occurs. By using these biosensors or analyzing devices, measurement is electrochemically conducted to accurately perform quantitative measurement in an immuno-chromatographic sensor that enables only a qualitative decision according to the related art. In all of the inventions, however, it is extremely difficult to provide biosensors made of materials of uniform properties and perform stable measurement in the biosensors, so that quantitative measurement with high accuracy cannot be achieved at all. Consequently, it is quite difficult to provide an immuno-chromatographic sensor that enables measurement anywhere at anytime by anyone.

The present invention has been devised to solve the problems. An object of the present invention is to provide an inexpensive biosensor that can perform measurement with high accuracy or convenience. In the biosensor where an immune reaction basically occurs, it is possible to improve the accuracy of measurement and enable measurement anywhere at anytime by anyone while keeping convenience as in an immuno-biosensor of the related art. Further, it is possible to realize an electrochemical analysis, enable measurement by reactions other than the immune reaction, and increase the accuracy of immunoassay or achieve simultaneous measurement of immunoassay items and the measuring items of an enzyme reaction.

Solution to Problem

In order to solve the problem, a biosensor of the present invention is a biosensor for qualitatively or quantitatively measuring a target analyte contained in a specimen solution, the biosensor including: an electrode sensor unit in which an electric conductive layer is provided on an electrode-unit forming substrate having an insulating property and an electrode portion for detecting an electrochemical signal is formed on the electrode-unit forming substrate; a chromatographic sensor unit including an extended layer for extending a specimen solution by a capillary flow; a specimen solution supply portion for receiving the specimen solution, the specimen solution supply portion being provided at one of a point facing the electrode portion and the extended layer and a point communicating with the electrode portion and the extended layer; and a reagent portion provided at least one point of the electrode sensor unit, the extended layer of the chromatographic sensor unit, and the specimen solution supply portion, wherein the electrode sensor unit and the chromatographic sensor unit are stacked.

With this configuration, it is possible to achieve a biosensor including the electrode sensor unit and the chromatographic sensor unit with the specimen solution supply portion shared by the electrode sensor unit and the chromatographic sensor unit. The sensor units have the reagent portion provided at least one point, and a reaction caused by a capillary flow on the extended layer can be measured at two points on the chromatographic sensor unit and the electrode sensor unit, respectively.

The specimen solution supply portion for receiving the specimen solution is provided at one of the point facing the electrode portion and the extended layer and the point communicating with the electrode portion and the extended layer. Thus even if the electrode sensor unit and the chromatographic sensor unit are not correctly stacked, the specimen solution is properly supplied to the electrode portion and the extended layer, and the measurement accuracy is not adversely affected on each portion of the electrode sensor unit and the chromatographic sensor unit.

Since the specimen solution is supplied to the electrode portion and the extended layer, it is possible to obtain information from the chromatographic sensor unit and information of an electrochemical signal from the electrode sensor unit, thereby improving the accuracy and convenience of the biosensor and increasing the number of measuring items.

For example, any items are available that include the detection of the position of the specimen solution on the extended layer by an electric signal, the detection of the addition of the specimen solution to the specimen solution supply portion, the detection of a hematocrit value (Hct) in blood serving as a specimen solution, and the correction of the degree of reaction.

The electrode-unit forming substrate having an insulating property is made of an insulating liquid impermeable material. The liquid impermeable material does not allow the permeation of a liquid into the material. For example, the liquid impermeable material is a synthetic resin material such as ABS, polystyrene, and polyvinyl chloride, a metal, or a glass. In the case of a liquid permeable material allowing the permeation of a liquid, e.g., a material such as paper, the permeation of a liquid can be prevented by coating the surface of the material with resin or a film or performing water repellent finishing.

The extended layer is a passage through which a specimen solution is extended by a capillary flow, and the extended layer includes a porous film or a small space formed by any member. Any component may be used that includes a membrane filter made of, e.g., nitrocellulose, filter paper made of glass fiber or cellulose, and a small space formed of, e.g., nanopillars.

The electric conductive layer may be formed using any material and any technique such as screen printing and sputtering.

The biosensor of the present invention, wherein the extended layer is provided on an extended-portion forming substrate having an insulating property, and the electrode sensor unit and the chromatographic sensor unit are stacked with the extended-portion forming substrate interposed between the electric conductive layer of the electrode sensor unit and the extended layer of the chromatographic sensor unit.

With this configuration, the electrode sensor unit and the chromatographic sensor unit are stacked with the extended-portion forming substrate interposed between the electric conductive layer of the electrode sensor unit and the extended layer of the chromatographic sensor unit. Thus it is possible to properly fabricate the biosensor including the two different types of sensors.

In the configuration of the sensor units, the extended-portion forming substrate is interposed between the electric conductive layer of the electrode sensor unit and the extended layer of the chromatographic sensor unit. Thus the electric conductive layer of the electrode sensor unit and the extended layer receiving a capillary flow do not directly come into contact with each other. With this configuration, the configurations and properties of the sensor units are not adversely affected and the sensor units can be independently provided.

The extended-portion forming substrate having an insulating property is made of an insulating liquid impermeable material. The liquid impermeable material does not allow the permeation of a liquid into the material. For example, the liquid impermeable material is a synthetic resin material such as ABS, polystyrene, and polyvinyl chloride, a metal, or a glass. In the case of a liquid permeable material allowing the permeation of a liquid, e.g., a material such as paper, the permeation of a liquid can be prevented by coating the surface of the material with resin or a film or performing water repellent finishing.

The electric conductive layer and the extended layer are stacked in this configuration. The electric conductive layer and the extended layer may be stacked with any adhesive for bonding interposed between the extended-portion forming substrate and the electric conductive layer.

The biosensor of the present invention further includes: reagent immobilizing portions on which a reagent specifically reacting with a target analyte is immobilized, the reagent immobilizing portions being provided partially on the extended layer; and a labeled reagent retaining portion that is provided partially on one of the specimen solution supply portion and the extended layer and retains a labeled reagent soluble in contact with the specimen solution and specifically reacting with the target analyte, wherein a target analyte component in the specimen solution is qualitatively or quantitatively measured by measuring the degree of reaction of the labeled reagent on the reagent immobilizing portions.

The labeled reagent is a reagent that is capable of specifically reacting with a target analyte and is labeled with a marker. Any markers may be used as long as various types of detection are possible. In a preferred embodiment of the present invention, the marker may be selected from enzymes, proteins, chromogens such as fluorescent substances, absorbing pigments, and luminescent materials, and insoluble particles such as metal colloids and latex particles.

In the labeled reagent retaining portion, any reagent other than the labeled reagent may be mixed with the labeled reagent.

The biosensor of the present invention, wherein the specimen solution is blood, a blood component is extended on the extended layer without being filtered, and at least one response value in the extended layer and at least one response value in the electrode portion are measurable.

With this configuration, the response value in the extended layer and the response value in the electrode portion can be obtained. Thus it is possible to improve the convenience and accuracy of the biosensor and increase the number of measuring items.

The biosensor of the present invention, wherein the reagent portion containing a reagent specifically reacting with any substance in the specimen solution is provided partially on the electrode portion, the reagent portion is capable of hydrating or dissolving in contact with the specimen solution, and any substance in the specimen solution is qualitatively or quantitatively measured by measuring the degree of reaction in the reagent portion as a current response value.

With this configuration, it is possible to qualitatively or quantitatively measure any substance in the specimen solution in an electrochemical manner.

The reagent is, e.g., an enzyme specifically reacting with any substance in the specimen solution. Further, any reagent may be used, e.g., a mediator for measuring the degree of reaction in an enzyme reaction as a current response value may be used or a reagent or an electrolyte for electron transfer may be used. The specimen solution comes into contact with the reagent of the reagent portion and hydration or dissolution occurs, so that a specific reaction occurs between a substance in the specimen solution and an enzyme in an environment suitable for a reaction of an electrolyte. Electrons generated by the enzyme reaction or necessary electrons are measured as a current response value in an electrode through a mediator.

Further, any substance such as glucose, cholesterol, and neutral fat in the specimen solution can be electrochemically measured.

The reagent configuration of the reagent portion does not always have to contain an enzyme, a mediator, and an electrolyte. The reagent configuration may be optionally changed according to a measured substance.

The biosensor of the present invention, wherein the reagent portion containing a reagent specifically reacting with a target analyte in the specimen solution is provided partially on the electrode portion and is capable of hydrating or dissolving in contact with the specimen solution, the biosensor further including: reagent immobilizing portions on which the reagent specifically reacting with the target analyte is immobilized, the reagent immobilizing portions being provided partially on the extended layer; and a labeled reagent retaining portion that is provided partially on one of the specimen solution supply portion and the extended layer and retains a labeled reagent soluble in contact with the specimen solution and specifically reacting with the target analyte, wherein any number of target analyte components in the specimen solution are qualitatively or quantitatively measured by measuring the degree of reaction in the reagent portion as a current response value and the degree of reaction of the labeled reagent in the reagent immobilizing portion.

This configuration makes it possible to measure, in the single biosensor, any number of electrochemically detectable substances and substances detected in an immune response measured by a chromatographic sensor.

ADVANTAGEOUS EFFECTS OF INVENTION

As has been discussed, according to the present invention, an electrode sensor unit and a chromatographic sensor unit are stacked with an extended-portion forming substrate interposed between the electric conductive layer of the electrode sensor unit and the extended layer of the chromatographic sensor unit. Thus in a fabrication process, even when an electrode portion is formed by screen printing, the extended layer is not deformed. Also in the fabrication of a biosensor, the electric conductive layer of the electrode portion and the extended layer do not come into contact with each other, so that even a solvent component remaining on the electrode portion does not adversely affect the extended layer. Thus the specimen solution can be sufficiently extended and the reliability of the biosensor can be satisfactorily maintained.

The specimen solution supply portion for receiving the specimen solution is provided at one of the point facing the electrode portion and the extended layer and the point communicating with the electrode portion and the extended layer. Thus even if the electrode sensor unit and the chromatographic sensor unit are not accurately stacked, the specimen solution is properly supplied to the electrode portion and the extended layer and the measurement accuracy is not adversely affected on each portion of the electrode sensor unit and the chromatographic sensor unit, thereby preventing a reduction in reliability.

Since the specimen solution is supplied to the electrode portion and the extended layer, it is possible to obtain information from the chromatographic sensor unit and information of an electrochemical signal from the electrode portion, thereby improving the accuracy and convenience of the biosensor and increasing the number of measuring items.

DESCRIPTION OF EMBODIMENTS

A biosensor according to an embodiment of the present invention will be specifically described below in accordance with the accompanying drawings. The embodiment is merely exemplary and the present invention is not limited to the embodiment.

Figure 1:
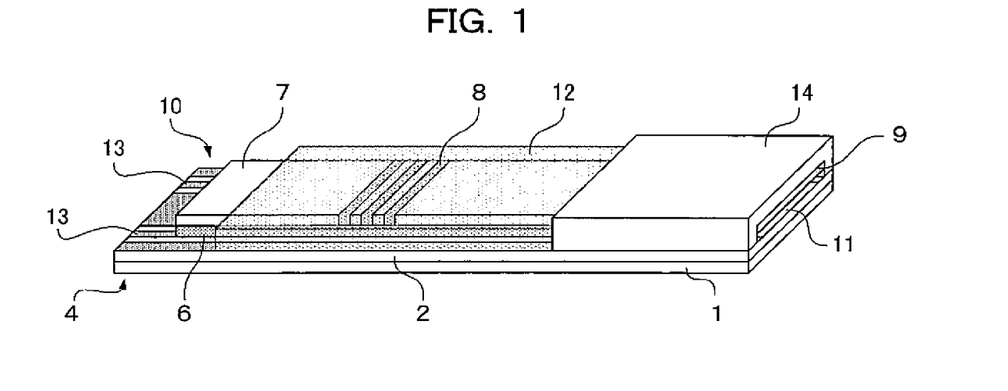
FIG. 1 is a perspective view showing a biosensor according to a first embodiment of the present invention.
Figure 2:
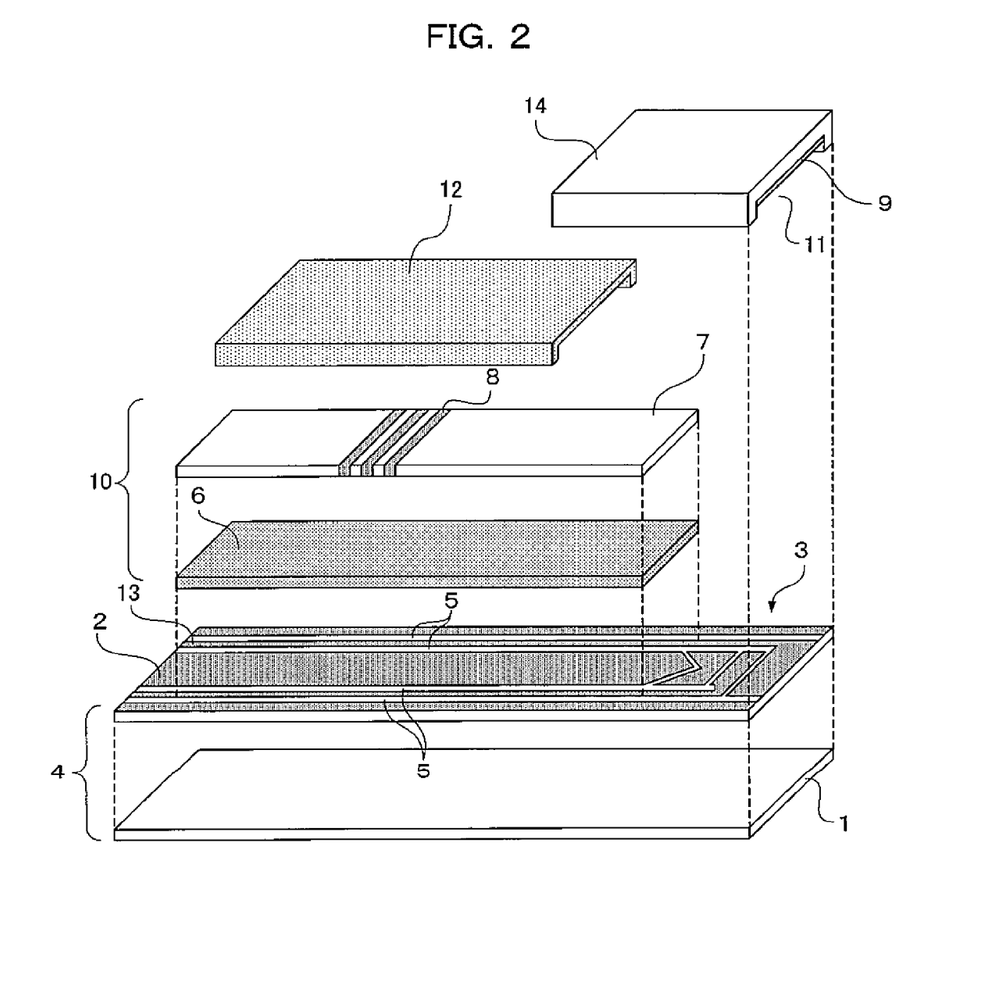
FIG. 2 is an exploded perspective view of the biosensor.

FIG. 1 is a perspective view showing the configuration of a biosensor according to a first embodiment. FIG. 2 is an exploded view showing the biosensor of FIG. 1.

As shown in FIGS. 1 and 2, in the biosensor according to the first embodiment of the present invention, an electrode sensor unit 4 and a chromatographic sensor unit 10 are stacked. The electrode sensor unit 4 and the chromatographic sensor unit 10 will be described later.

The electrode sensor unit 4 is configured as follows: an electric conductive layer 2 is provided on an electrode-unit forming substrate 1 having an insulating property, and the electric conductive layer 2 is divided by slits 5 such that an electrode portion 3 for detecting an electrochemical signal and an electrode terminal portion 13 are formed partially on the electrode-unit forming substrate 1.

The chromatographic sensor unit 10 is configured as follows: reference numeral 6 in FIGS. 1 and 2 denotes an extended-portion forming substrate on which an extended layer 7 is provided. The extended layer 7 includes a porous film for extending a specimen solution such as blood through a capillary flow. Partially on the extended layer 7, reagent immobilizing portions 8 are provided on which a specific protein serving as a reagent is immobilized. The chromatographic sensor unit 10 is made up of the extended layer 7 on which the reagent immobilizing portions 8 are provided, the extended-portion forming substrate 6, and a labeled reagent retaining portion 9 that will be described later.

The electrode portion 3 is disposed at one end of the electrode sensor unit 4. Above the electrode portion 3, a space forming member 14 is attached and a clearance 11 that serves as a specimen solution supply portion for receiving a specimen solution such as blood is formed between the space forming member 14 and the electrode portion 3. The underside of the clearance 11 faces the electrode portion 3 of the electrode sensor unit 4 and a rear point of the clearance 11 faces one end (an upstream-side end in an extending direction) of the extended layer 7. Partially in the clearance 11, the labeled reagent retaining portion 9 is provided that retains a labeled reagent soluble in contact with the specimen solution. The labeled reagent retaining portion 9 may be provided on a part of the extended layer 7 (upstream of the reagent immobilizing portions 8 in the extending direction) and the labeled reagent retaining portion 9 may contain any reagent other than the labeled reagent. In the present embodiment, the top surface of the extended layer 7 is covered with a transparent liquid impermeable sheet 12.

Particularly, in the biosensor according to the embodiment of the present invention, the electrode sensor unit 4 and the chromatographic sensor unit 10 are stacked with the extended-portion forming substrate 6 interposed between the electric conductive layer 2 of the electrode sensor unit 4 and the extended layer 7 of the chromatographic sensor unit 10.

The biosensor is used by inserting and connecting the other end of the electrode sensor unit 4, on which the electrode terminal portion 13 and so on are formed, into an analyzing apparatus (not shown). In a state in which the biosensor is attached to the analyzing apparatus, a specimen solution such as blood is dropped (added) to the clearance 11 serving as a specimen solution supply portion. When the biosensor is attached to the analyzing apparatus, the attachment of the biosensor can be detected by a change of an electric signal during the energization of the circuit of the electrode sensor unit 4 in the biosensor. After that, the dropping (addition) of the specimen solution to the attached biosensor can be detected by a change of the electric signal from the electrode sensor unit 4.

In this configuration, when a specimen solution such as blood is dropped (added) to the clearance 11, the specimen solution reacts, is extended, and is measured in the chromatographic sensor unit 10. For example, in the present embodiment, a hematocrit value is simultaneously measured from a current response value in the electrode portion 3.

In the chromatographic sensor unit 10, when blood serving as a specimen solution is added and introduced into the clearance 11, the blood dissolves a labeled reagent on the labeled reagent retaining portion 9 in the clearance 11. In response to the dissolution of the labeled reagent, a labeled antibody and a target analyte (antigen) of the specimen solution are bounded specifically to each other, penetrate the extended layer 7 in a chromatography downstream direction, and reach the reagent immobilizing portion 8. The complex of the labeled antibody and the antigen is specifically bound to an antibody immobilized on the reagent immobilizing portion 8 of the extended layer 7. Through these processes, the color of the labeled antibody on the reagent immobilizing portion 8 is detected by a visual inspection or the analyzing apparatus using an optical detection method. Thus it is possible to confirm the presence of a target analyte in the specimen solution or the concentration of the target analyte.

As has been discussed, when a specimen solution such as blood is dropped (added) from the electrode sensor unit 4, a current response value is measured on the electrode portion 3 and any measuring item such as a hematocrit value is measured.

Thus it is possible to obtain information (response value) from the chromatographic sensor unit 10 and information (response value) of the electrochemical signal from the electrode sensor unit 4, thereby improving the accuracy of the biosensor. In the present embodiment, a CRP concentration in data (including the CRP concentration) measured in the chromatographic sensor unit 10 is corrected based on data (including a hematocrit value) measured in the electrode sensor unit 4, so that the measurement accuracy of the CRP concentration is increased. In other words, the measured concentration value of a target analyte such as CRP in the chromatographic sensor unit 10 may be adversely affected by other factors (e.g., a hematocrit value (blood viscosity)), resulting in fluctuations in measurement accuracy, whereas in the present embodiment, the concentration is corrected based on a hematocrit value measured in the electrode sensor unit 4, thereby increasing the measurement accuracy of the concentration of a target analyte.

The connection of the biosensor to the analyzing apparatus is detected by the electric signal from the electrode sensor unit 4 and the addition of blood as a specimen solution into the clearance 11 is detected by the electric signal from the electrode sensor unit 4, thereby improving convenience. For example, as compared with the case where the analyzing apparatus is operated by a manual input of the attachment of the biosensor to the analyzing apparatus and the dropping of the specimen solution to the biosensor, it is possible to eliminate the need for the inputting operation and improve convenience. Since the attachment and dropping can be automatically detected without delay, it is possible to correctly and automatically detect the attachment of the biosensor, an extension start time, and a measurement time without causing a time lag, unlike in the manual input, thereby improving reliability.

In the case where an item different from the measuring items of the chromatographic sensor unit 10 is measured in the electrode sensor unit 4, the number of measuring items may be increased.

With this configuration, the electrode sensor unit 4 and the chromatographic sensor unit 10 are stacked with the extended-portion forming substrate 6 interposed between the electric conductive layer 2 of the electrode sensor unit 4 and the extended layer 7 of the chromatographic sensor unit 10. Thus in the fabrication process, the electric conductive layer and the extended layer 7 are separately formed. Even when the electrode portion 3 is formed by screen printing, a printing paste does not come into the extended layer 7 including the porous film, so that the extended layer 7 is not deformed or broken in such a manner as to hamper a capillary flow. Further, in the fabrication of the biosensor, when the electrode sensor unit 4 and the chromatographic sensor unit 10 are stacked, the extended-portion forming substrate 6 is interposed between the electric conductive layer 2 of the electrode sensor unit 4 and the extended layer 7 of the chromatographic sensor unit 10 and thus the electric conductive layer 2 of the electrode sensor unit 4 does not directly come into contact with the extended layer 7 including the porous film. With this configuration, even a solvent component remaining on the electric conductive layer 2 does not adversely affect the extended layer 7 including the porous film. Thus it is possible to satisfactorily maintain the reliability of the biosensor.

The chromatographic sensor unit 10 and the electrode sensor unit 4 are simply stacked, each of which is subjected to a measuring operation, the clearance 11 serving as a specimen solution supply portion for receiving a specimen solution such as blood is located at a point facing the electrode portion 3 and the extended layer 7, and the measuring operations are performed simultaneously in the chromatographic sensor unit 10 and the electrode sensor unit 4. With this configuration, even if the electrode sensor unit 4 and the chromatographic sensor unit 10 are incorrectly stacked, the specimen solution is properly supplied to the electrode portion 3 and the extended layer 7, and the measurement accuracy is not adversely affected on each portion of the electrode sensor unit 4 and the chromatographic sensor unit 10. In the flow-through type of Patent Literature 2, the measuring constituent elements including the sample inlet, the impregnating portions, the passage member, the electrode portion, the specific binding substance insolubilizing passage, the absorbing portion, and the lower substrate are stacked in the thickness direction and a sample is passed in the thickness direction. In this case, unless the antibody insolubilizing porous film and the electrode that have been separately prepared are stacked with high accuracy, the quantitative accuracy considerably declines. In the embodiment of the present invention, such a problem does not occur.

In the present embodiment, blood serving as a specimen solution is directly introduced to the electrode portion 3 and the extended layer 7 from the clearance 11 serving as a specimen solution supply portion. The present invention is not limited to this configuration. A connecting path allowing the passage of the specimen solution may be provided between the clearance 11 serving as a specimen solution supply portion and the electrode portion 3 (or the extended layer 7), and the specimen solution may flow into the electrode portion 3 and the extended layer 7 through the connecting path.

The extended layer 7 includes the porous film, which is merely exemplary. The extended layer 7 may be made of any material as long as any specimen solution can be extended through a capillary flow.

Figure 3:
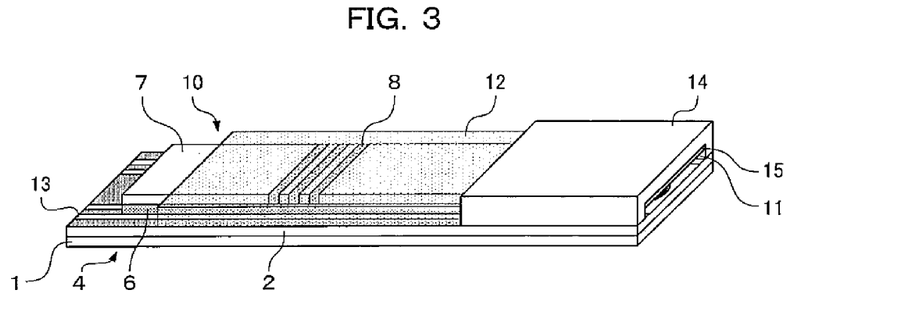
FIG. 3 is a perspective view showing a biosensor according to a second embodiment of the present invention.
Figure 4:
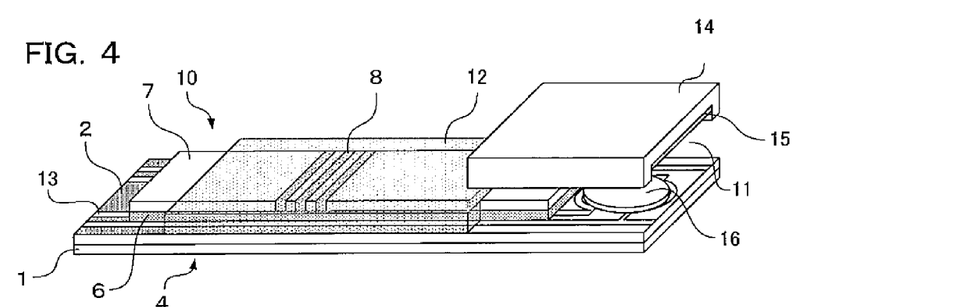
FIG. 4 is a partially exploded perspective view of the biosensor.
Figure 5:
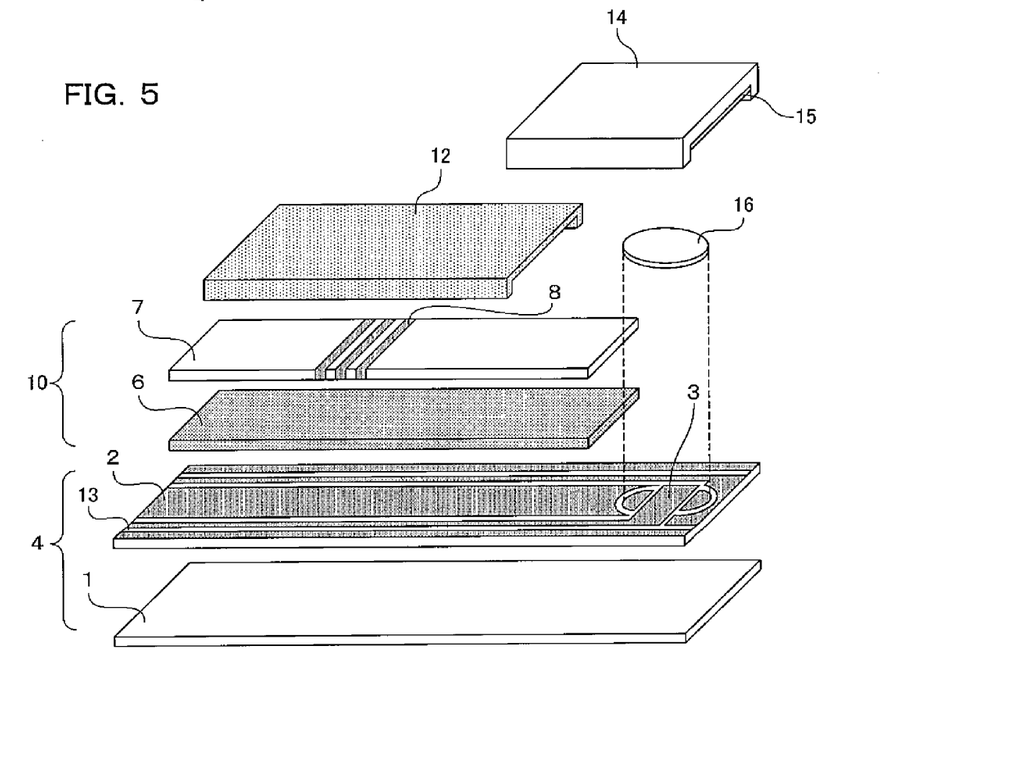
FIG. 5 is an exploded perspective view of the biosensor.

In the present embodiment, blood is directly supplied to the electrode portion 3 and the extended layer 7. The present invention is not limited to this configuration. As shown in FIGS. 3 to 5, in a biosensor of a second embodiment, a clearance 11 has a cell shrinkage reagent 15 that constricts blood cell components such as red blood cells and white blood cells in blood supplied to the clearance 11. Plasma components are properly introduced into an extended layer 7 and an extension speed in the extended layer 7 is increased. Further, a reagent portion 16 contains a reagent that can specifically react with any substance in a specimen solution. The reagent portion 16 reads, as a current response value, the degree of reaction of a substance in the specimen solution with the reagent, so that qualitative or quantitative measurement is possible. The reagent portion 16 contains at least any one of reagents necessary for reading an electrical response value, e.g., an enzyme, a mediator, a substrate, and an electrolyte.

Moreover, as shown in FIGS. 3 to 5, the reagent portion 16 may be provided on the top surface of an electrode portion 3. The reagent portion 16 contains a reagent specifically reacting with any substance or a target analyte in the specimen solution, and a component having reacted in the reagent portion 16 may be measured on the electrode portion 3. The reagent portion 16 can hydrate or dissolve in contact with the specimen solution. The degree of reaction in the reagent portion 16 is measured as a current response value, so that any substance in the specimen solution can be qualitatively or quantitatively measured.

Also in the present embodiment, as in the embodiment of FIGS. 1 and 2, reagent immobilizing portions 8 are provided partially on the extended layer 7. On the reagent immobilizing portions 8, the reagent specifically reacting with a target analyte is immobilized. As shown in FIGS. 3 to 5, the reactive reagent portion 16 provided on the top surface of the electrode portion 3 or in the clearance 11 contains a labeled reagent that is soluble in contact with the specimen solution and specifically reacts with a target analyte. Any number of target analyte components in the specimen solution may be qualitatively or quantitatively measured by measuring the degree of reaction in the reagent portion 16 as a current response value and the degree of reaction of the labeled reagent in the reagent immobilizing portions 8. It is not always necessary to place the labeled reagent, which is soluble in contact with the specimen solution and specifically reacts with the target analyte, on the top surface of the electrode portion 3 or in the clearance 11. The labeled reagent may be placed upstream of the reagent immobilizing portions 8 on the extended layer 7.

In the configurations of FIGS. 1 to 5, any bonding method and technique may be used and any problems do not occur.

Figure 6:
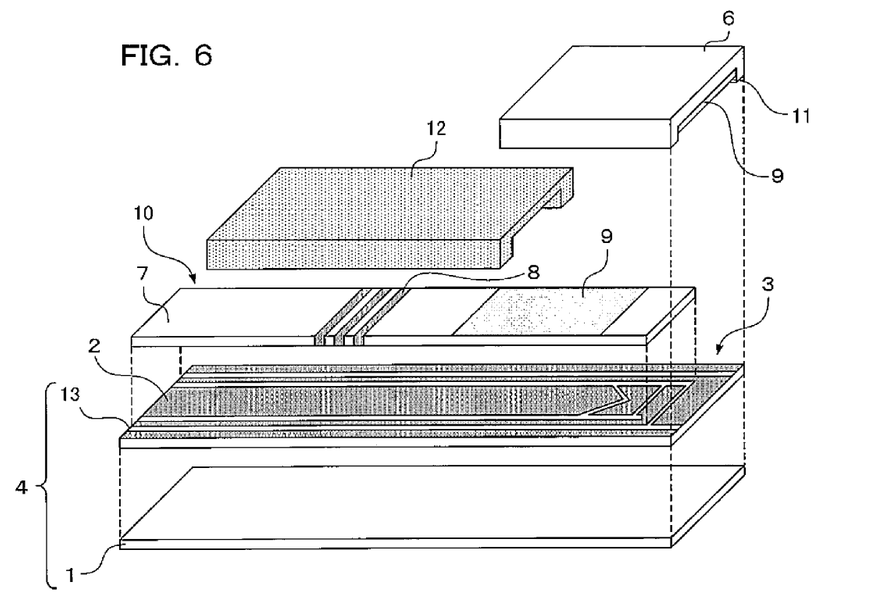
FIG. 6 is an exploded perspective view showing a biosensor according to a third embodiment of the present invention.
Figure 7:
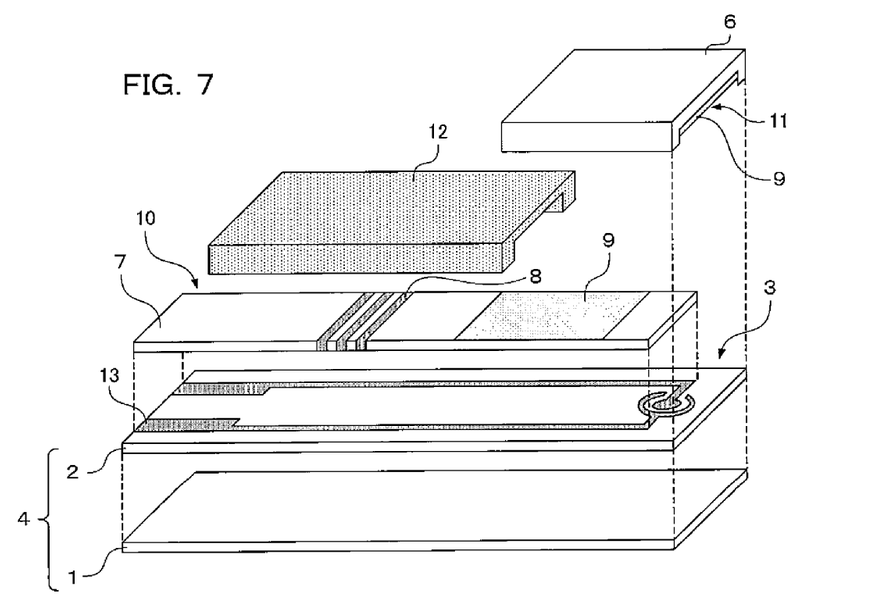
FIG. 7 is an exploded perspective view showing another biosensor according to the third embodiment of the present invention.

FIGS. 6 and 7 show examples of a biosensor according to a third embodiment in which an electric conductive layer 2 having an electrode portion 3 is provided on an electrode-unit forming substrate 1 having an insulating property and an extended layer 7 including a porous film is provided on the surface of the electric conductive layer 2. In the biosensors of FIGS. 6 and 7, the extended layer 7 is formed after the electric conductive layer 2 is provided. Even when the electric conductive layer 2 is formed by a technique such as printing, the electrode portion 3 can be formed with high accuracy and the influence of an organic solvent or the like in, e.g., a printing paste can be eliminated, unlike in the formation of the electric conductive layer 2 on the surface of the extended layer 7. Moreover, it is not necessary to bond the electric conductive layer 2 and the extended layer 7 to each other, eliminating the need for increasing the accuracy of bonding.

Since the extended layer is formed directly on the electric conductive layer, the position of a specimen solution extended on the extended layer can be detected by an electrical response value.

In this case, the electrode portion 3 may be fabricated before or after the formation of the extended layer 7. After the electric conductive layer 2 and the extended layer 7 are formed, a sensor configuration including reagent immobilizing portions 8 and a labeled reagent retaining portion 9 may be formed.

Figure 8:
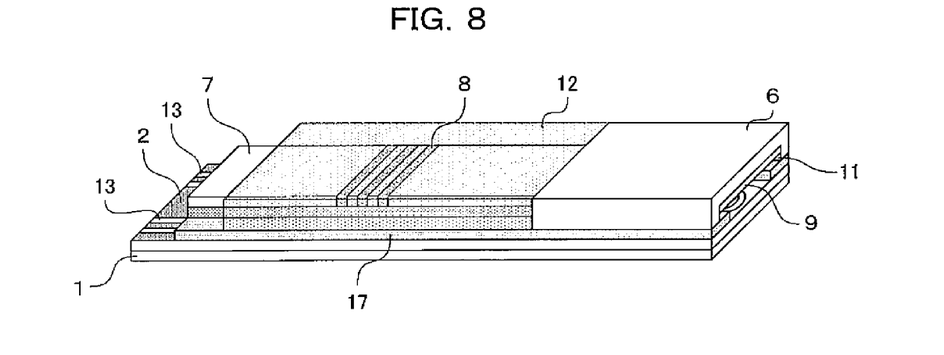
FIG. 8 is a perspective view showing still another biosensor according to the third embodiment of the present invention.
Figure 9:
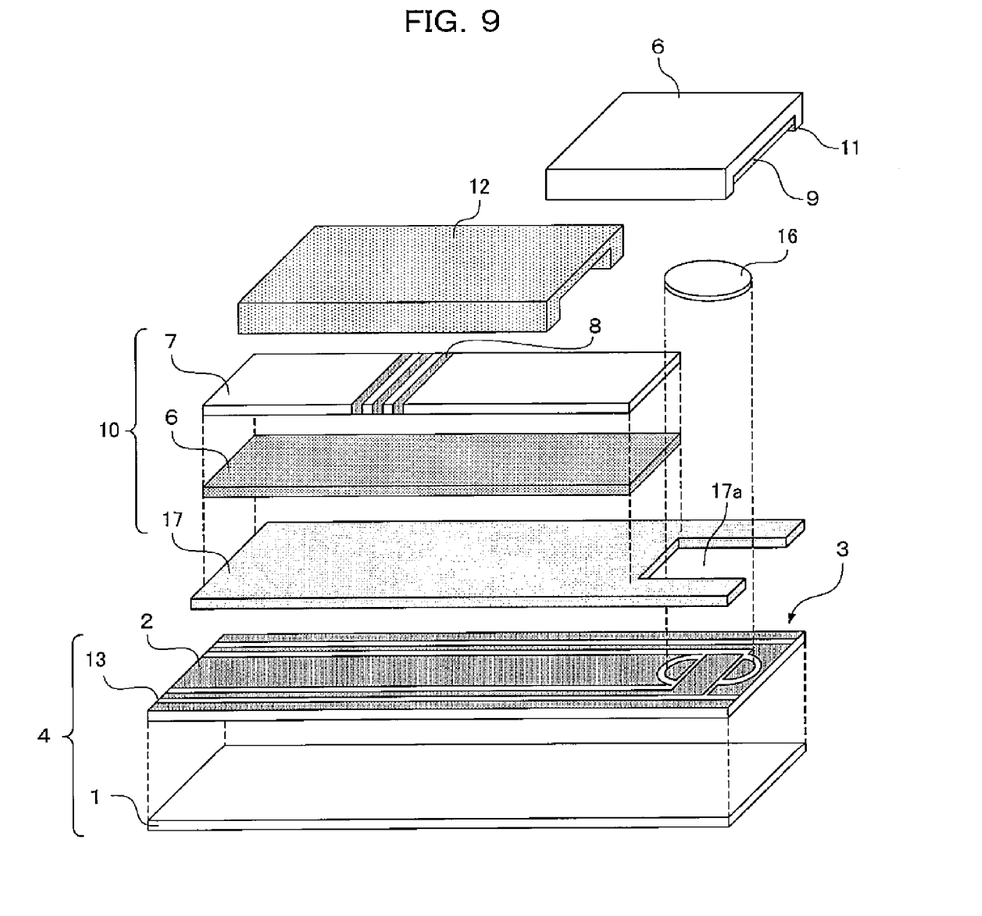
FIG. 9 is an exploded perspective view of the biosensor.

FIGS. 8 and 9 show an example of a biosensor in which a sheet material 17 is provided between an electrode sensor unit 4 and a chromatographic sensor unit 10. The sensor units are bonded to each other via the sheet material 17. The sheet material 17 has an adhesive for bonding the sensor units 4 and 10. The adhesive may be any bonding material such as an adhesive substance, a thermoplastic, and a photo-curing resin, and any bonding method such as ultrasonic bonding may be used. The sheet material 17 may have any shape, e.g., a shape (a recessed portion in FIGS. 8 and 9) 17a that restricts the area of an electrode portion 3.

The first to third embodiments are merely exemplary and the present invention is not always limited to these embodiments.

Industrial Applicability

The biosensor of the present invention is useful as a biosensor for a POCT analyzing apparatus.

The invention claimed is:

1. A biosensor for qualitatively or quantitatively measuring a target analyte contained in a specimen solution, the biosensor comprising:
   an electrode sensor unit including an electrode-unit forming substrate having an insulating property, an electric conductive layer provided on the electrode-unit forming substrate, and an electrode portion formed on the electrode-unit forming substrate for detecting an electrochemical signal;
   a chromatographic sensor unit including an extended-portion forming substrate having an insulating property and an extended layer disposed on the extended-portion forming substrate for extending a specimen solution by a capillary flow;
   a specimen solution supply portion for receiving the specimen solution, the specimen solution supply portion being provided at one of (a) a point facing the electrode portion and the extended layer and (b) a point communicating with the electrode portion and the extended layer; and a reagent portion provided at least one point of the electrode sensor unit, the extended layer of the chromatographic sensor unit, and the specimen solution supply portion, wherein the electrode sensor unit and the chromatographic sensor unit are stacked, and wherein the extended-portion forming substrate is interposed between the electric conductive layer of the electrode sensor unit and the extended layer of the chromatographic sensor unit.

2. The biosensor according to claim 1, further comprising:

reagent immobilizing portions on which a reagent specifically reacting with a target analyte is immobilized, the reagent immobilizing portions being provided partially on the extended layer; and a labeled reagent retaining portion that is provided partially on one of the specimen solution supply portion and the extended layer and retains a labeled reagent soluble in contact with the specimen solution and specifically reacting with the target analyte, wherein a target analyte component in the specimen solution is qualitatively or quantitatively measured by measuring a degree of reaction of the labeled reagent on the reagent immobilizing portions.

3. The biosensor according to claim 1, wherein the extended layer allows a blood component to be extended thereon without being filtered, and at least one response value in the extended layer and at least one response value in the electrode portion are measurable.

4. The biosensor according to claim 1, wherein the reagent portion containing a reagent specifically reacting with any substance in the specimen solution is provided partially on the electrode portion, the reagent portion is capable of hydrating or dissolving in contact with the specimen solution, and any substance in the specimen solution is qualitatively or quantitatively measured by measuring a degree of reaction in the reagent portion as a current response value.

5. The biosensor according to claim 1, wherein the reagent portion containing a reagent specifically reacting with a target analyte in the specimen solution is provided partially on the electrode portion and is capable of hydrating or dissolving in contact with the specimen solution, the biosensor further comprising:

reagent immobilizing portions on which the reagent specifically reacting with the target analyte is immobilized, the reagent immobilizing portions being provided partially on the extended layer; and a labeled reagent retaining portion that is provided partially on one of the specimen solution supply portion and the extended layer and retains a labeled reagent soluble in contact with the specimen solution and specifically reacting with the target analyte, wherein any number of target analyte components in the specimen solution are qualitatively or quantitatively measured by measuring a degree of reaction in the reagent portion as a current response value and a degree of reaction of the labeled reagent in the reagent immobilizing portion.

* * * * *